(12) United States Patent
Bogren et al.

(10) Patent No.: US 11,214,902 B2
(45) Date of Patent: Jan. 4, 2022

(54) ABSORBENT MATERIAL

(71) Applicant: ESSITY HYGIENE AND HEALTH AKTIEBOLAG, Gothenburg (SE)

(72) Inventors: Maria Bogren, Gothenburg (SE); Lars Fingal, Gothenburg (SE); Anna Nihlstrand, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 902 days.

(21) Appl. No.: 15/777,373

(22) PCT Filed: Nov. 20, 2015

(86) PCT No.: PCT/SE2015/051252
§ 371 (c)(1),
(2) Date: May 18, 2018

(87) PCT Pub. No.: WO2017/086851
PCT Pub. Date: May 26, 2017

(65) Prior Publication Data
US 2021/0198823 A1 Jul. 1, 2021

(51) Int. Cl.
*D04H 5/06* (2006.01)
*D21H 13/14* (2006.01)
(Continued)

(52) U.S. Cl.
CPC .............. *D04H 5/03* (2013.01); *D04H 5/06* (2013.01); *D21H 13/14* (2013.01); *D21H 13/24* (2013.01);
(Continued)

(58) Field of Classification Search
CPC ........ D21H 13/08; D21H 27/00; D21H 13/14; D21H 13/24; D21H 27/02; D21H 27/002;
(Continued)

(56) References Cited

U.S. PATENT DOCUMENTS

| 4,808,467 | A | * | 2/1989 | Suskind | D21H 27/34 28/104 |
| 4,902,564 | A | * | 2/1990 | Israel | D21H 27/30 28/104 |

(Continued)

FOREIGN PATENT DOCUMENTS

| EP | 1 550 754 A1 | 7/2005 |
| EP | 1 689 923 A2 | 8/2006 |

(Continued)

OTHER PUBLICATIONS

Herbert Holik, "Chapter 3, Chemical Additives," Handbook of Paper and Board, Wiley-VCH, 2006, ISBN: 3-524-30997-7, 3.6.6.3, p. 92.

(Continued)

*Primary Examiner* — Jose A Fortuna
(74) *Attorney, Agent, or Firm* — Wood Herron & Evans LLP

(57) ABSTRACT

An absorbent material, such as a non-woven web or a tissue paper, includes continuous filaments and short fibers, the short fibers including natural and/or synthetic fibers or staple fibers. The absorbent material exhibits an absorbency speed of equal to or less than 2 s and a weight loss when washed of equal to or less than 5%. The absorbent material can be incorporated into a wipe.

10 Claims, 1 Drawing Sheet

(51) Int. Cl.
    *D21H 13/24*     (2006.01)
    *D21H 21/20*     (2006.01)
    *D21H 27/00*     (2006.01)
    *D21H 27/02*     (2006.01)
    *D04H 5/03*     (2012.01)

(52) U.S. Cl.
    CPC ........... *D21H 21/20* (2013.01); *D21H 27/007* (2013.01); *D21H 27/02* (2013.01)

(58) Field of Classification Search
    CPC .......... D21H 27/34; D04H 1/492; D04H 5/03; D04H 5/06; B31F 1/07; B32B 5/26; B32B 9/02; Y10T 442/689
    See application file for complete search history.

(56) References Cited

U.S. PATENT DOCUMENTS

| | | | | |
|---|---|---|---|---|
| 6,163,943 | A * | 12/2000 | Johansson | D04H 1/4374 28/104 |
| 6,550,115 | B1 * | 4/2003 | Skoog | D04H 1/498 28/104 |
| 7,422,660 | B2 | 9/2008 | Billgren et al. | |
| 7,432,219 | B2 * | 10/2008 | Strandqvist | D04H 5/03 442/401 |
| 8,133,825 | B2 * | 3/2012 | Bunyard | D04H 1/64 442/118 |
| 8,389,427 | B2 * | 3/2013 | Gustafsson | D04H 1/4334 442/408 |
| 9,822,487 | B2 * | 11/2017 | Ahoniemi | D04H 1/495 |
| 9,863,073 | B2 * | 1/2018 | Stralin | D04H 1/492 |
| 2005/0022954 | A1 * | 2/2005 | Strandqvist | D21F 11/00 162/115 |
| 2005/0112980 | A1 * | 5/2005 | Strandqvist | D04H 5/03 442/416 |
| 2005/0159065 | A1 * | 7/2005 | Stralin | D04H 5/03 442/327 |
| 2007/0232178 | A1 | 10/2007 | Polat et al. | |
| 2010/0075120 | A1 | 3/2010 | Gustafsson et al. | |
| 2015/0322606 | A1 * | 11/2015 | Stralin et al. | D04H 3/011 442/59 |
| 2015/0330004 | A1 * | 11/2015 | Stralin et al. | D06C 23/04 428/156 |
| 2017/0022667 | A1 * | 1/2017 | Ahoniemi | D21H 13/08 |
| 2021/0198823 | A1 * | 7/2021 | Bogren | A61Q 19/00 |

FOREIGN PATENT DOCUMENTS

| | | | |
|---|---|---|---|
| EP | 2692924 A1 | 2/2014 | |
| JP | 2006-52498 A | 2/2006 | |
| WO | WO-99/23290 A1 | 5/1999 | |
| WO | WO-2005/042819 A2 | 5/2005 | |
| WO | WO-2008/066417 A1 | 6/2008 | |
| WO | WO-2008066417 A1 * | 6/2008 | .............. D04H 3/02 |
| WO | WO-2012/150902 A1 | 11/2012 | |
| WO | WO-2013/095241 A1 | 6/2013 | |
| WO | WO-2014/104956 A1 | 7/2014 | |
| WO | WO-2017086851 A * | 5/2017 | ............. D21H 13/14 |

OTHER PUBLICATIONS

Extended European search report dated Jun. 5, 2019 issued in European patent application No. 15 90 8898.8.

Chinese Patent Office, Second Office Action issued in CN 201580084687.4 dated Dec. 7, 2020 with English translation (12 pages).

Chilean First Examination Report dated Nov. 15, 2018 issued in Chileanen patent application No. 201801351 (8 pages) and its partial English-language translation thereof (2 pages).

\* cited by examiner

ABSORBENT MATERIAL

CROSS-REFERENCE TO PRIOR APPLICATION

This application is a § 371 National Stage Application of PCT International Application No. PCT/SE2015/051252 filed Nov. 20, 2015, which is incorporated herein in its entirety.

TECHNICAL FIELD

The present disclosure relates to an absorbent material, such as a non-woven web or a tissue paper, including continuous filaments and short fibers, the short fibers including natural and/or synthetic fibers or staple fibers.

The present disclosure also relates to a method for manufacturing the absorbent material and a wipe including the absorbent material.

BACKGROUND

It is known in the art to make disposable hand towels and disposable house hold towels. These can either be supplied as singular sheets or on a roll. The consumer will when desiring to use a towel for cleaning hands or surfaces or the like, pull out a single sheet from the dispenser or rip a sheet from a roll, use it for wiping and then dispose of it. However, the use of disposable absorbent articles, although having its advantages, from for instance a hygienic point of view, has its draw backs from an environmental and logistical point of view.

On the other hand, it is known to produce dish rags that can be rinsed and washed multiple times. Even though they perform well from an environmental and logistical standpoint, they work less well from a hygienic and aesthetical point of view, becoming stained and attracting dirt and bacteria.

It has therefore been suggested to solve this problem by making hand towels and household towels that is possible to rinse and reuse a few times before discarding. To be able to make ordinary disposable absorbent articles from either tissue or nonwoven material, washable, either a binder has to be added to the absorbent material or thermo-bonding or mechanical bonding has to be employed. Unfortunately, the introduction of these techniques has the disadvantage of reducing the absorbency of the material.

Thus, there is a need for a material exhibiting both good absorbency properties as well as being able to wash and reuse.

SUMMARY

In an embodiment, an absorbent material, such as a non-woven web or a tissue paper, includes continuous filaments and short fibers, the short fibers including pulp fibers and/or staple fibers, wherein the absorbent material exhibits an absorbency speed when measured with ISO 12625-8, of equal to or less than 2 s and a weight loss when washed in the Washing Machine Test as described herein, of equal to or less than 5%.

In an embodiment, the absorbent material exhibits an absorbency of at least 5 g/g.

In an embodiment, the absorbent material includes the pulp fibers in an amount of at least 5 wt %, at least 30 wt %, or at least 50 wt %, of the absorbent material.

In an embodiment, the filaments have a diameter of 15 µm or less.

In an embodiment, the absorbent material further includes a wet strength agent in the amount of, 0.2-1.0 wt %.

In an embodiment, the staple fibers have a length of 5-20 mm, or 5-12 mm.

In an embodiment, the staple fibers are polylactic fibers, regenerated cellulose such as viscose and lyocell fibers, pulp fibers, cotton fibers, hemp fibers, flax fibers, polypropylene fibers, polyester fibers or bicomponent fibers.

In an embodiment, the natural fibers are pulp fibers, cotton fibers, hemp fibers, or flax fibers.

In an embodiment, the continuous filaments are polylactic acid, polypropylene or polyethylene terephthalate filaments.

In an embodiment, the absorbent material is hydroentangled.

In an embodiment, the absorbent material is embossed.

BRIEF DESCRIPTION OF THE DRAWINGS

Embodiments of the invention will be more closely described with reference to the enclosed figures.

DETAILED DESCRIPTION OF PARTICULAR EMBODIMENTS

Figure 1:
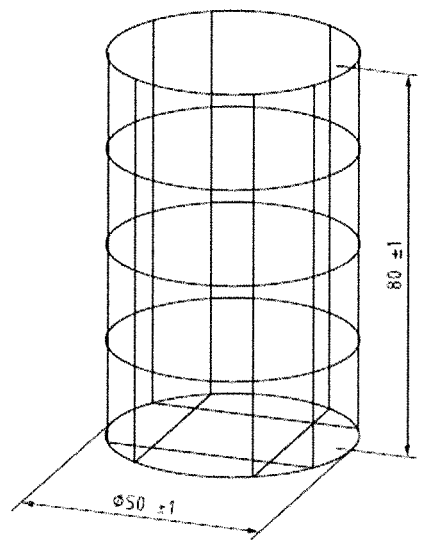
FIG. 1 shows the cylindrical basket specification for the water absorbency time and capacity measurement.

The absorbent material includes a mixture of continuous spunlaid filaments and short fibers including natural fibers and/or staple fibers. These different types of fibers as well as other details of embodiments of the invention are defined as follows.

Continuous Filaments

Filaments are fibers that in proportion to their diameter are very long, in principle endless. They can be produced by melting and extruding a thermoplastic polymer through fine nozzles, thereafter the polymer will be cooled, for example by the action of an air flow blown at and along the polymer streams, and solidified into strands that can be treated by drawing, stretching or crimping. Chemicals for additional functions can be added to the surface. Filaments can also be produced by chemical reaction of a solution of fiber-forming reactants entering a reagence medium, e g by spinning of viscose fibers from a cellulose xanthate solution into sulphuric acid.

Meltblown filaments are produced by extruding molten thermoplastic polymer through fine nozzles in very fine streams and directing converging air flows towards the polymers streams so that they are drawn out into continuous filaments with a very small diameter. Production of meltblown is e.g., described in U.S. Pat. Nos. 3,849,241 or 4,048,364. The fibers can be microfibers or macrofibers depending on their dimensions. Microfibers have a linear density of less than 1 dtex.

Spunbond filaments are produced in a similar way, but the air flows are cooler and the stretching of the filaments is done by air to get an appropriate diameter. The fiber diameter is usually above 10 µm, usually 10-100 µm. Production of spunbond is e.g., described in U.S. Pat. Nos. 4,813,864 or 5,545,371.

Spunbond and meltblown filaments are as a group called spunlaid filaments, meaning that they are directly, in situ, laid down on a moving surface to form a web that further on in the process is bonded. Controlling the 'melt flow index' by choice of polymers and temperature profile is an essential part of controlling the extruding and thereby the filament formation. The spunbond filaments normally are stronger and more even.

Tow is another source of filaments, which normally is a precursor in the production of staple fibers, but also is sold and used as a product of its own. In the same way as with spunlaid fibers, fine polymer streams are drawn out and stretched, but instead of being laid down on a moving surface to form a web, they are kept in a bundle to finalize drawing and stretching. When staple fibers are produced, this bundle of filaments is then treated with spin finish chemicals, normally crimped and then fed into a cutting stage where a wheel with knives will cut the filaments into distinct fiber lengths that are packed into bales to be shipped and used as staple fibers. When tow is produced, the filament bundles are packed, with or without spin finish chemicals, into bales or boxes.

Any thermoplastic polymer that has enough coherent properties to let itself be drawn out in this way in the molten state, can in principle be used for producing meltblown or spunbond fibers. Examples of useful polymers are polyolefins, such as polypropylene and polyethylene, or polyesters including polylactic acid. Copolymers of these polymers may of course also be used, as well as natural polymers with thermoplastic properties.

The continuous filaments can be based on any polylactic acid, PLA (polylactic acid) polymer. PLA filaments based on a homogeneous polylactic acid resin comprising a mono polymer and have essentially the same melting point throughout the PLA filaments. However, other polymers and copolymers and polymers with additives based on PLA can of course be used.

Natural Fibers

There are many types of natural fibers that can be used, especially those that have a capacity to absorb water and tendency to help in creating a coherent sheet. Among the natural fibers possible to use, there are primarily the cellulosic fibers such as seed hair fibers, e.g., cotton, kapok, and milkweed; leaf fibers e g sisal, abaca, pineapple, and New Zealand hemp; or bast fibers e.g., flax, hemp, jute, kenaf, and pulp.

Cellulose from wood pulp fibers is especially well suited to use, and both softwood fibers and hardwood fibers are suitable, and also recycled fibers can be used.

The pulp fiber lengths will vary from around 3 mm for softwood fibers and around 1.2 mm for hardwood fibers and a mix of these lengths, and even shorter, for recycled fibers.

Staple Fibers

The staple fibers used can be produced from the same substances and by the same processes as the filaments discussed above. Other usable staple fibers are those made from regenerated cellulose such as viscose and lyocell. Staple fibers could also be any fiber with a fiber length greater than 2 mm, but not being a continuous filament.

They can be treated with spin finish and crimped, but this is not necessary for the type of processes used to produce the material described in the present disclosure. Spin finish and crimp is normally added to ease the handling of the fibers in a dry process, e.g., a card, and/or to give certain properties, e.g. hydrophilicity, to a material consisting only of these fibers, e.g., a nonwoven topsheet for a diaper.

The cutting of the fiber bundle normally is done to result in a single cut length, which can be altered by varying the distances between the knives of the cutting wheel. Depending on the planned use different fiber lengths are used, between 2-18 mm are known to be used.

For hydroentangled materials made by traditional wetlaid technology, the strength of the material and its properties like surface abrasion resistance are increased as a function of the fiber length (for the same thickness and polymer of the fiber).

When continuous filaments are used together with staple fibers and pulp, the strength of the material will mostly come from the filaments.

Bicomponent Fibers

Bicomponent fibers according to embodiments of the invention can be of any type, such as core/sheet type or side by side. They may be made of polyester, polypropylene, polyethylene, polylactic acid, polyamide or co-polymers thereof. The different materials can be arbitrarily chosen as core/sheet and in arbitrarily order when the bicomponent fiber is of side by side type.

Process

One general example of a method for producing the absorbent material according to embodiments of the present invention includes the steps of:

Providing an endless forming fabric, where the continuous filaments can be laid down, and excess air be sucked off through the forming fabric, to form the precursor of a web, advancing the forming fabric with the continuous filaments to a wetlaying stage, where a slurry including a mixture of short fibers including natural fibers and/or staple fibers is wetlaid on and partly into the precursor web of continuous filaments, and excess water is drained off through the forming fabric, advancing the forming fabric with the filaments and fiber mixture to a hydroentangling stage, where the filaments and fibers are mixed intimately together and bonded into an absorbent material by the action of many thin jets of high-pressure water impinging on the fibers to mix and entangle them with each other, and entangling water is drained off through the forming fabric, advancing the forming fabric to a drying stage (not shown) where the absorbent material is dried, and further advancing the absorbent material to stages for embossing, rolling, cutting, packing, etc.

The continuous filaments made from extruded molten thermoplastic pellets may be laid down directly on a forming fabric where they are allowed to form an un-bonded web structure in which the filaments can move relatively freely from each other. This can be achieved by making the distance between the nozzles and the forming fabric relatively large, so that the filaments are allowed to cool down before they land on the forming fabric, at which lower temperature their stickiness is largely reduced. Alternatively, cooling of the filaments before they are laid on the forming fabric is achieved in some other way, e.g., by means of using multiple air sources where air is used to cool the filaments when they have been drawn out or stretched to the desired degree.

The air used for cooling, drawing and stretching the filaments is sucked through the forming fabric, to let the filaments follow the air flow into the meshes of the forming fabric to be stayed there. A good vacuum might be needed to suck off the air.

The speed of the filaments as they are laid down on the forming fabric is much higher than the speed of the forming fabric, so the filaments will form irregular loops and bends as they are collected on the forming fabric to form a very randomized precursor web. The continuous spun-laid filaments are extruded from a spinnerette with a speed of more than 2000 m/min and less than 6000 m/min or more than 3000 m/min and less than 5000 m/min when drawn by the slot attenuator. The velocity of the forming web or the transport web is about 100-300 m/min. The velocity of the continuous filament in the slot attenuation unit is at least ten times higher than the velocity of the forming wire, one example is a velocity of about 2500 m/min and a speed of the forming wire of about 200 m/min.

The pulp and/or staple fibers are slurried in a conventional way, either mixed together or first separately slurried and then mixed, and conventional papermaking additives such as wet and/or dry strength agents, retention aids, dispersing agents, are added, to produce a well-mixed slurry of short fibers in water.

This mixture is pumped out through a wet-laying headbox onto the moving forming fabric where it is laid down on the un-bonded precursor filament web with its freely moving filaments. The short fibers will stay on the forming fabric and the filaments. Some of the fibers will enter between the filaments, but the vast majority of them will stay on top of the filament web. The excess water is sucked through the web of filaments laid on the forming fabric and down through the forming fabric, by means of suction boxes arranged under the forming fabric.

Hydroentangling

The fibrous web of continuous filaments and staple fibers and pulp is hydroentangled while it is still supported by the forming fabric and is intensely mixed and bonded into a composite nonwoven material. An instructive description of the hydroentangling process is given in CA patent no. 841 938.

In the hydroentangling stage, the different fiber types will be entangled and a composite nonwoven material is obtained in which all fiber types are substantially homogeneously mixed and integrated with each other. The fine mobile spunlaid filaments are twisted around and entangled with themselves and the other fibers which give a material with a very high strength. The energy supply needed for the hydroentangling is relatively low, i.e. the material is easy to entangle. The energy supply at the hydroentangling is appropriately in the interval 50-500 kWh/ton.

In particular embodiments, no bonding, by e.g., thermal bonding or hydroentangling, of the precursor filament web should occur before the short fibers and/or are laid down. The filaments should be completely free to move in respect of each other to enable the staple and pulp fibers to mix and twirl into the filament web during entangling. Thermal bonding points between filaments in the filament web at this part of the process would act as blockings to stop the staple and pulp fibers to enmesh near these bonding points, as they would keep the filaments immobile in the vicinity of the thermal bonding points. The 'sieve effect' of the web would be enhanced and a more two-sided material would be the result. As used herein, "no thermal bondings" means that there are substantially no points where the filaments have been excerted to heat and pressure, e.g., between heated rollers, to render some of the filaments pressed together such that they will be softened and/or melted together to deformation in points of contact. Some bond points could, especially for meltblown, result from residual tackiness at the moment of laying-down, but these will be without deformation in the points of contact, and would probably be so weak as to break up under the influence of the force from the hydroentangling water jets.

The strength of a hydroentangled material based on only staple and/or pulp will depend heavily on the amount of entangling points for each fiber; thus long staple fibers, and long pulp fibers, are preferred. When filaments are used, the strength will be based mostly on the filaments, and reached fairly quickly in the entangling. Thus, most of the entangling energy will be spent on mixing filaments and fibers to reach a good integration. The unbonded open structure of the filaments according to embodiments of the invention will greatly enhance the ease of this mixing.

The pulp fibers are irregular, flat, twisted and curly and get pliable when wet. These properties will let them fairly easily be mixed and entangled into and also stuck in a web of filaments, and/or longer staple fibers. Thus, pulp can be used with a filament web that is pre-bonded, even a pre-bonded web that can be treated as a normal web by rolling and unrolling operations, even if it still does not have the final strength to its use as a wiping material.

The entangling stage can include several transverse bars with rows of nozzles from which very fine water jets under very high pressure are directed against the fibrous web to provide an entangling of the fibers. The water jet pressure can then be adapted to have a certain pressure profile with different pressures in the different rows of nozzles.

Alternatively, the fibrous web can, before hydroentangling, be transferred to a second entangling fabric. In this case, the web can also, prior to the transfer, be hydroentangled by a first hydroentangling station with one or more bars with rows of nozzles.

Drying Etc.

The hydroentangled wet web is then dried, which can be done on conventional web drying equipment, for example of the types used for tissue drying, such as through-air drying or Yankee drying. The material is after drying normally wound into mother rolls before converting. The material is then converted in known ways to suitable formats and packed. The structure of the material can be changed by further processing such as microcreping, hot calandering, etc. To the material can also be added different additives such as wet strength agents, binder chemicals, latexes, debonders, etc. The structure of the material can now be changed by the embossing described.

Composite Nonwoven Material

A composite nonwoven according to embodiments of the invention can be produced with a total basis weight of 40-120 g/m$^2$.

The unbonded filaments will improve the mixing-in of the short fibers, such that even a short fiber will have enough entangled bonding points to keep it securely in the web. The secure bonding will result in very good resistance to abrasion. The short fibers will result in an improved material as they have more fiber ends per gram fiber and are easier to move in the Z-direction (perpendicular to web plane). More fiber ends will project from the surface of the web, thus enhancing the textile feeling. However, the greatest effect of a soft feel is the embossing process.

Wet Strength Agent

The wet strength agent can be a cationic polymer containing cationic groups, such as positively charged quaternary nitrogen atoms. The wet strength agent can be selected from, but is not limited to urea-formaldehyde resins, melamine-formaldehyde resins, polyvinyl amine, polyureide-formaldehyde resins, glyoxal-acrylamide resins and cationic materials obtained by the reaction of polyalkylene polyamines with polysaccharides such as starch and various natural gums, as well as 3-hydroxyazetidinium ion-containing resins, which are obtained by reacting nitrogen-containing polymers with epichlorohydrine. The above materials are mentioned in U.S. Pat. No. 3,998,690 where also references for their disclosure are found.

Embossing

A well-known technique to increase the thickness of a paper product is to emboss the paper web. Any embossing can lead to embossed elements all having the same height or to embossing elements having different heights. An embossing process may be carried out in the nip between an embossing roll and an anvil roll.

The embossing roll is formed of a hard material, usually metal, especially steel, but there is also known embossing rolls made of hard rubber or hard plastics materials. The embossing roll can have protrusions on its circumferential surface leading to so-called embossed depressions in the web or it can have depressions in its circumferential surface leading to so-called embossed protrusions in the web.

Anvil rolls may be softer than the corresponding embossing roll and may consist of rubber, such as natural rubber, or plastic materials, paper or steel. However, structured anvil rolls, especially rolls made of paper, rubber or plastics materials or steel are also known. Said smooth backing roll may be a steel roll or a rubber roll, said rubber roll having hardness between 50 and 90 shore according to ASTM D2240. The hardness of the rubber chosen depends on the pressure applied and is between 50 and 95 Shore A. In embodiment, the hardness has a value of about 45 to 60 Shore A. Typically, the embossing work is much better with lower values on hardness in order to get a three dimensional in the structure and a deep embossing, typically 55 Shore A has been used. The combination of a high embossing structure together with a lower value of the hardness makes it possible to achieve the impressed stable embossing according to embodiments of the present invention. It is also good that the material web can be pushed and pressed down into the rubber such that the web is deformed.

All above described methods have the following common features: the first embossing roll is formed of a hard material, usually metal, especially steel, but there are also known embossing rolls made of hard rubber or hard plastics materials. The embossing rolls can be a male roll having individual protrusions. Alternatively, the embossing roll can be a female roll with individual embossing depressions. Typical depths of embossing patterns are between 0.8 mm and 1.4 mm. The embossing performed here is due to the desired stiffness of the filaments rather rough and heavy and therefore the embossing is performed with an embossing roll having protuberances or protrusions corresponding to the second areas of the web material with a height or depth in the range of from 1.5 mm to 3.5 mm, or about 2.5 mm. This together with the stable deformation of the filaments induced into the web material also results in rather high bulk of the web material.

Another embossing technique includes a steel embossing roll and a corresponding anvil steel roll (so-called Union embossing). The surfaces of these rolls are being formed in such a manner that deformation of the web is achieved within one single embossing step.

The embossing not only serves to provide bulk to the fibrous nonwoven product but in this case also to provide an improved strength to the product. The strength of a product is important for consumer products. The conventional reason for embossing is in addition to create bulk, to generate higher absorbency or improved perceived softness.

The embossing is performed without applying any heat. There might be some heat generated by the embossing since pressure is applied, and frictional forces may give raise to some heat, however no heat is added to the process as such. The embossing may be performed using heat as well.

An example of the embossing is that it is made with a depth of the embossing protrusions of about 2.5 mm against an anvil roll of a hardness of 55 Shore A. The repeat height is 13.3 mm and the repeat width is 5.7 mm and the embossing figure is an oval of 3.8×2.2 mm and a depth of 2.5 mm. Every other row of oval embossments is aligned and the rows in between are centrally offset in the middle and in turn also aligned by every other row. The oval has its length in the machine direction of the web material. But of course, the present invention is not restricted to any specific embossing pattern, but any embossing pattern can be used. The embossed area is about 10 percent but can optionally be anything from 3 to 20 or even 50%, for example between 10 and 30%. In fact, as the embossing is not destructive, the embossed area can be chosen rather freely.

The softness of the anvil roll together with the height of the embossing protrusion is a combination that has carefully been elaborated and is important in order to get the three dimensional structure in the material web. Further, the amount of embossing spots in an area can also influence. In the above mentioned example, there are 2.9 spots per $cm^2$.

The invention may be embodied in many different forms and should not be construed as limited to the embodiments set forth in the description thereto.

EXAMPLES

Test Procedures:
ABSORPTION CAPACITY, DIN 54 540 (Modified)
(a) Purpose and Field of Application
To decide a material's ability to hold fluid. Used for both tissue and nonwoven.
(b) Definition
(c) Principle
A weighted test sample is soaked in water during 60 seconds, then hung to drip of under 120 seconds, and weighted thereafter.
(d) Apparatus
Stop-watch
Scale with an accuracy of ±0.01 g
Beaker, 3000 ml, low model with a flat bottom
Paper clamps which fixate the test sample in 3 spots
(e) Sample Preparation
Material consumption: Approx. 0.1 $m^2$ distributed over the material.
Number of samples: 5 pieces
Preparation: The samples are punched into squares in both MD and CD with the side 100±0.5 mm.
Conditioning: 23° C., 50% RH in at least 4 h
De-ionized water, temperature of 23 degrees
The water shall be changed after each test batch (5 samples)
(f) Procedure
A material which includes several layers should be tested as a whole product. The sample is weighed to an accuracy of 0.01 g. Thereafter it is attached with the paper clip intended for DIN 54 540, so that the sample is attached in three points. The machine direction of the sample should be vertical when hung. A bowl with a flat bottom is filled with liquid and the sample is submerged for 60±3 seconds to then be hung up to drip for 120±3 seconds. It is important that the sample hangs freely and straight during the dewatering. After 120 seconds the sample is released from the clip and re-weighed with an accuracy of 0.01 g.
(g) Calculation and Expression of Results
The weight of the sample before and after wetting is measured, the absorption is calculated according to the below formula and a mean value for the absorption is calculated for the samples.

$$\text{Absorption} = \frac{m_v - m_t}{m_t} [g/g]$$

$m_v$=the mass of the wet sample [g]
$m_t$=the mass of the dry sample [g]
Report the mean value with the accuracy of one decimal.

(h) Reference
Original method: DIN 54 540, part 4
Deflection from the Reference Method:
Soaking of the sample is different from the original method, where the sample is put horizontally, but in this case is hung vertically.

WATER ABSORPTION TIME AND CAPACITY, ISO 12625-8 (Basket Absorption)

(i) Purpose and Field of Application
The purpose is to determine the water absorption time and the water absorption capacity of tissue paper and finished tissue products using the basket immersion method manually.

(j) Definition
Ply Independently formed unit of unlaminated tissue, like that made directly from a tissue machine.
Sheet Unit of a laminated or unlaminated tissue, like that present in the finished tissue product.
Water absorption time The time it takes for a test piece to become completely wetted [s]
Water absorption Amount of water the test piece is able to absorb
capacity [g water/g material in test piece]

(k) Principle
A test piece of defined width and total mass is placed in a cylindrical basket which is dropped from a defined height over a water surface. The time is measured from that the basket is dropped until the test piece has been fully wetted and the results serve as water absorption time. The amount of absorbed water is determined from the dry and wet weight of the test piece.

Figure 2:
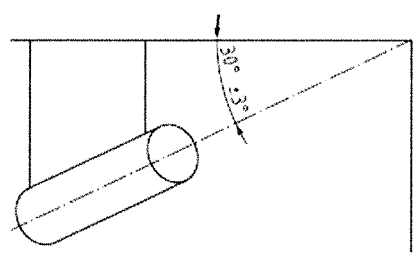
FIG. 2 shows the draining position for the basket used in the absorbency time and capacity measurement.

(l) Equipment
Steel wired basket, weight 3.0±0.1 g, diameter 50±1 mm, height 80±1 mm (see FIG. 1)
Water container, volume at least 3 liters (minimum depth of water 100 mm)
Balance with an accuracy of 0.001 g
Draining equipment, so that the basket can hang at a 30±3° angle with the horizontal (see FIG. 2)
Timer(s) with accuracy of 0.1 s
Deionized water, conductivity≤0.25 mS/m at 25° C., in accordance with ISO 14487

(m) Sample Preparation
Prepare the test pieces by cutting the material in machine direction to a width of 76±1 mm and enough length so that the total mass of each test piece is 5.0±0.2 g. If more than one sheet is needed, all sheets should have the top side up. If several sheets are cut at once, separate them before testing. Select the test pieces randomly from the entire test specimen. Cut enough material for 5 observations for an official LAB test reports.

(i) Conditioning
Condition the prepared samples for minimum 2 hours at 23° C. and 50% rel. humidity. Note: in ISO 14187 it is stated that a conditioning time of 4 h is sufficient, however, prepared tissue samples have been found to condition within 2 h. Not mandatory for production control, however a stable and controlled climate is necessary.

(n) Procedure Record the Mass of the Test Piece to the Nearest 0.01 g.
Dry test piece mass=$m_0$
Record the mass of the basket to the nearest 0.01 g. Basket mass=$m_b$
Roll the test piece so that they fit in the basket without folding it and place it in the basket (Use of a pen can help). It should be loosely packed in the basket.
Position the basket with test piece at a height of 25±5 mm from the water surface, keeping it horizontal and parallel to the water surface.
Release the basket into the water and start the timer at the same time.
Stop the timer when the test piece is completely immersed in the water even if it has not yet sunk to the bottom. Record the wetting time to the nearest 0.1 s.
Allow the basket to remain in the water for 30±1 s, and then take it out in a horizontal position.
Hang the basket at 30±3° angle and let it drain for 60±1 s.
Carefully place the basket on the scale and record the mass of the basket with the wetted sample to the nearest 0.01 g. Basket mass+wet sample mass=$m_n$
Repeat for the remaining test pieces. Carefully wipe down the basket between test pieces. It is recommended to change the water after five tests.

(o) Calculation and Expression of Results
Calculate the water absorption capacity, $W_a$:

$$W_a = \frac{m_n - m_0 - m_b}{m_0}$$

where
$m_n$=basket mass+wet sample mass [g]
$m_0$=dry test piece mass [g]
$m_b$=basket mass [g]
Calculate the average value and standard deviation of the readings for both water absorption time and water absorption capacity.

(i) Results Reporting
Water absorption time is reported in seconds [s] to the nearest 0.1 s.
Water absorption capacity is reported in grams water per gram test piece [g/g] to the nearest 0.1 g/g.
All deviations from this method must be noted in the report.

(ii) Typical Standard Deviations (Relative Standard Deviation; Coefficient of Variation):
10% RSD for water absorption time.
3% RSD for water absorption capacity.

(p) Validation
A production site or laboratory is considered qualified when passing a t-test on 95% confidence level compared with an R&D-laboratory or another qualified laboratory, and regular re-qualifications are made with comparative measurements among sites.

(q) Reference
ISO 12625-8:2011 Water-absorption time and water-absorption capacity, basket-immersion test method
ISO 14487 Pulps—Standard water for physical testing
ISO 187—Standard atmosphere for conditioning and testing tissue WASHING MACHINE TEST
The loss of weight when washed was measured using the Washing Machine Test according to the following:

(r) Purpose and Field of Application

To determine the ability and durability of a cleaning cloth when using and rinsing the cloth repeatedly with water. This method is suited for semi-disposable nonwoven products as the strain on the material is high. A wash machine is used to have repeatability in the method as well as have a similar use as by hand.

(s) Definition

Determination of the ability to wash a semi-disposable cleaning cloth.

(t) Principle

Each sample is weighed in before each test run. A fixed program as described below for the washing machine will run 4-6 samples at a time representing the rinsing and abrasion of the material. During the run in the machine an amount of material will be lost depending on the integrity of the material. Weighing the samples after each test will reveal how much material has been lost and also the visual assessment can be made as documentation is done afterwards as well.

(u) Level (v) Equipment

Washing machine: The washing machine on which the test samples were washed was a Cylinda, model FT44.

Analytical scale

Punch, 230×230 mm (w) Sample Preparation

Material required: 0.27 m²

Randomly select 5 samples and punch them out of the 0.27 m² material piece. Samples containing wet strength agent, were heat treated 30 min in 80° C. before testing, to secure sufficient curing.

(x) Procedure

Each sample is marked with water resistant pen and weighed

Each sample was put into the washing machine

The washing machine was set for the program for "quick color 30° C.", and set it to 34 min. running time The remaining water was gently squeezed out of the samples and samples were separated from each other and dried on a bench over night at a temperature of 23 degrees C., 50% RH, for 12 h.

Each sample was weighed and the loss of material was calculated and reported as percentage loss of material (y) Calculation and Expression of Results The loss of material was calculated in grams (g) and also the loss of material in % of the original mass of each sample. The mean value of the weight loss of the samples of each was calculated.

Results

Samples

Sample A

The test sample A consisted of a wet-laid pulp (70 wt % of the absorbent material) polylactide filaments (25 wt % of the absorbent material) having a diameter of 16.8 (mean value of 20 measurements) and 12 mm long, 1.7 dtex, polylactide staple fibers (Type 260, 1.7 dtex from Trevira) (5 wt % of the absorbent material). The material has a grammage of 60 gsm and contains 0.3 wt % of a PAE type wet strength agent (Kymene GHP 020 from Solenis)). The material is hydroentangled. After hydroentangling the wet strength agent is sprayed onto the sample.

Sample B

The test sample B consisted of a wet-laid pulp (70 wt % of the absorbent material) polylactide filaments (25 wt % of the absorbent material) having a diameter of 14.3 μm (mean value of 20 measurements) and 12 mm long, 1.7 dtex, polylactide staple fibers (5 wt % of the absorbent material).

The material has a grammage of 62.4 gsm and contains 0.65 wt % of a PAE type wet strength agent (Kymene GHP 020 from Solenis). The material is hydroentangled. After hydroentangling the wet strength agent is sprayed onto the sample.

Sample C

The test sample C consisted of a wet-laid pulp (70 wt % of the absorbent material) polylactide filaments (25 wt % of the absorbent material) having a diameter of 14.3 μm (mean value of 20 measurements) and 1.7 dtex, 12 mm long polylactide staple fibers and 1.7 dtex, 6 mm long, viscose staple fibers (1.5% viscose and 3.5% polylactide fibers of the absorbent material). The material has a grammage of 66.2 gsm and contains 0.65 wt % of a PAE type wet strength agent (Kymene GHP 020 from Solenis). The material is hydroentangled. After hydroentangling the wet strength agent is sprayed onto the sample.

Sample D

The test sample D consisted of a wet-laid pulp (70 wt % of the absorbent material) polylactide filaments (25 wt % of the absorbent material) having a diameter of 14.3 μm (mean value of 20 measurements) and 5 mm long, 1.0 dtex, bicomponent fibers (polyethylene terephthalate (PET)/polyethylene (PE) (PET being core, PE being sheet) staple fibers (5 wt % of the absorbent material). The material has a grammage of 65.6 gsm and contains 0.65 wt % of a PAE type wet strength agent (Kymene GHP 020 from Solenis). The material is hydroentangled. After hydroentangling the wet strength agent is sprayed onto the sample.

Furthermore, the commercially available material Duramax (Kimberly-Clark) was tested. The material has a grammage of 65.5 gsm (bought in 2014 in Colombia). The absorption and washing machine test results are shown below in Table 1.

TABLE 1

| Sample | Absorption speed (s) | Total absorption (g/g) | Washing machine test weight loss (%) |
|---|---|---|---|
| A | 1.40 | 5.40 | 13.6 |
| B | 1.30 | 5.80 | 3.4 |
| C | 1.30 | 5.60 | 2.1 |
| D | 1.50 | 5.40 | 1.0 |
| Duramax | 6.50 | 4.80 | 0 |

The invention claimed is:

1. An absorbent material, comprising continuous filaments and short fibers, the short fibers comprising pulp fibers and/or staple fibers, and a wet strength agent in an amount of 0.2-1.0 wt % of the absorbent material, wherein the continuous filaments have a diameter less than or equal to 15 μm and the pulp fibers are present in an amount of at least 5 wt % of the absorbent material, wherein the absorbent material exhibits an absorbency speed when measured with ISO 12625-8, of equal to or less than 2 s and a weight loss when washed in the Washing Machine Test, of equal to or less than 5%, and wherein the absorbent material is hydroentangled.

2. The absorbent material according to claim 1, wherein the absorbent material further exhibits an absorbency of at least 5 g/g.

3. The absorbent material according to claim 1, wherein the pulp fibers are present in an amount of at least 30 wt % of the absorbent material.

4. The absorbent material according to claim 1, wherein the staple fibers have a length of 5-20 mm.

5. The absorbent material according to claim 1, wherein the staple fibers are, at least one of, polylactic fibers, regenerated cellulose fibers, pulp fibers, cotton fibers, hemp fibers, flax fibers, polypropylene fibers, polyester fibers or bicomponent fibers.

6. The absorbent material according to claim 1, wherein the short fibers are, at least one of, pulp fibers, cotton fibers, hemp fibers, or flax fibers.

7. The absorbent material according to claim 1, wherein continuous filaments are, at least one of, polylactic acid, polypropylene or polyethylene terephthalate filaments.

8. The absorbent material according to claim 1, wherein the absorbent material is embossed.

9. A wipe comprising the absorbent material according to claim 1.

10. The absorbent material according to claim 1, wherein the Washing Machine Test includes providing a plurality of samples each having about 0.27 m$^2$ of the absorbent material, weighing each of the samples, washing each of the samples together for a wash cycle in a washing machine, separating and drying the samples after the wash cycle, and re-weighing each of the samples after drying the samples to allow for a calculation of a loss of material caused during the washing, wherein the weight loss for the samples is less than or equal to 5% based on the material composition and construction of the absorbent material.

* * * * *